(12) United States Patent
Holm et al.

(10) Patent No.: US 11,007,086 B2
(45) Date of Patent: May 18, 2021

(54) WOUND DRESSING WITH MULTIPLE ADHESIVE LAYERS

(71) Applicant: 3M INNOVATIVE PROPERTIES COMPANY, Saint Paul, MN (US)

(72) Inventors: David R. Holm, Hudson, WI (US); Simon S. Fung, Woodbury, MN (US); James M. Sieracki, Brooklyn Center, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 570 days.

(21) Appl. No.: 15/539,866

(22) PCT Filed: Dec. 28, 2015

(86) PCT No.: PCT/US2015/067655
§ 371 (c)(1),
(2) Date: Jun. 26, 2017

(87) PCT Pub. No.: WO2016/109418
PCT Pub. Date: Jul. 7, 2016

(65) Prior Publication Data
US 2017/0367896 A1 Dec. 28, 2017

Related U.S. Application Data

(60) Provisional application No. 62/112,714, filed on Feb. 6, 2015, provisional application No. 62/098,058, filed on Dec. 30, 2014.

(51) Int. Cl.
*A61F 13/02* (2006.01)
*A61L 15/42* (2006.01)
(Continued)

(52) U.S. Cl.
CPC .... *A61F 13/0253* (2013.01); *A61F 13/00063* (2013.01); *A61F 13/0206* (2013.01);
(Continued)

(58) Field of Classification Search
CPC ................ A61F 13/00; A61F 13/00021; A61F 13/00029; A61F 13/00042;
(Continued)

(56) References Cited

U.S. PATENT DOCUMENTS

RE24,906 E 12/1960 Ulrich
3,389,827 A 6/1968 Abere
(Continued)

FOREIGN PATENT DOCUMENTS

CN 1756519 4/2006
CN 102196790 9/2011
(Continued)

OTHER PUBLICATIONS

International Search Report for PCT International Application No. PCT/US2015/067655, dated Apr. 22, 2016, 5 pages.

*Primary Examiner* — Rachael E Bredefeld
*Assistant Examiner* — Rachel A Berezik
(74) *Attorney, Agent, or Firm* — 3M Innovative Properties Company; Trisha D. Adamson (57) ABSTRACT

A wound dressing is provided. The wound dressing includes a moisture-transmissible backing layer having a first major surface, a second major surface, and a backing layer perimeter; an absorbent hydrophilic adhesive adhered to at least a portion of the second major surface of the backing layer, the absorbent hydrophilic adhesive comprising an absorbent hydrophilic adhesive perimeter; an antimicrobial agent disposed in the absorbent hydrophilic adhesive; a porous layer having a first side adhered to the absorbent hydrophilic adhesive, a second side, and a porous layer perimeter; and a
(Continued)

second hydrophobic adhesive adhered to the second side of the porous layer. The second major surface has a first hydrophobic adhesive disposed thereon proximate the backing layer perimeter. 100% of the absorbent hydrophilic adhesive perimeter is overlapped by the backing layer. At least 50% of the porous layer perimeter is overlapped by the absorbent hydrophilic adhesive.

16 Claims, 3 Drawing Sheets

(51) Int. Cl.
    *A61L 15/60*     (2006.01)
    *B32B 3/00*     (2006.01)
    *A61L 15/46*     (2006.01)
    *A61F 13/00*     (2006.01)
    *A61L 15/22*     (2006.01)
    *A61L 15/44*     (2006.01)
    *A61L 15/58*     (2006.01)
    *A61L 15/24*     (2006.01)
    *A61L 15/26*     (2006.01)

(52) U.S. Cl.
    CPC ...... *A61F 13/0216* (2013.01); *A61F 13/0266* (2013.01); *A61L 15/22* (2013.01); *A61L 15/24* (2013.01); *A61L 15/26* (2013.01); *A61L 15/425* (2013.01); *A61L 15/44* (2013.01); *A61L 15/46* (2013.01); *A61L 15/58* (2013.01); *A61L 15/60* (2013.01); *B32B 3/00* (2013.01); *A61L 2300/404* (2013.01)

(58) Field of Classification Search
    CPC .......... A61F 13/00046; A61F 13/00063; A61F 13/02; A61F 13/0203; A61F 13/0206; A61F 13/0209; A61F 13/0213; A61F 13/022; A61F 13/0226; A61F 13/025; A61F 13/0253; A61F 2013/00089; A61F 2013/00102; A61F 2013/00119; A61F 2013/00127; A61F 2013/00319; A61F 2013/00323; A61F 2013/00544; A61F 2013/00582; A61F 2013/00604; A61F 2013/00608; A61F 2013/00612; A61F 2013/00421; A61F 2013/00561; A61F 2013/00655; A61F 2013/00659; A61F 2013/00663; A61F 2013/00676; A61F 2013/00685; A61F 2013/00689; A61F 2013/00697; A61F 2013/0071; A61F 2013/00731; A61F 2013/0074; A61F 2013/00744; A61F 2013/00748; A61F 2013/00753; A61F 2013/00757; A61F 2013/00761; A61F 2013/00765; A61F 2013/0077; A61F 2013/00774; A61F 2013/00778; A61F 2013/00782; A61F 2013/00804; A61F 2013/00812; A61F 13/0223
    See application file for complete search history.

(56) References Cited

U.S. PATENT DOCUMENTS

| | | | |
|---|---|---|---|
| 3,645,835 A | 2/1972 | Hodgson | |
| 4,112,213 A | 9/1978 | Waldman | |
| 4,310,509 A | 1/1982 | Berglund | |
| 4,323,557 A | 4/1982 | Rosso | |
| 4,595,001 A | 6/1986 | Potter | |
| 4,737,410 A | 4/1988 | Kantner | |
| 4,931,282 A | 6/1990 | Asmus | |
| 4,969,880 A | 11/1990 | Zamierowski | |
| 5,088,483 A | 2/1992 | Heinecke | |
| 5,160,315 A | 11/1992 | Heinecke | |
| 5,225,473 A | 7/1993 | Duan | |
| 5,244,457 A * | 9/1993 | Karami | A61F 13/0226 602/43 |
| 5,261,893 A | 11/1993 | Zamierowski | |
| 5,389,376 A | 2/1995 | Duan | |
| 5,409,966 A | 4/1995 | Duan | |
| 5,527,293 A | 6/1996 | Zamierowski | |
| 6,071,267 A | 6/2000 | Zamierowski | |
| 6,171,985 B1 | 1/2001 | Joseph | |
| 6,242,665 B1 | 6/2001 | Malowaniec | |
| 6,368,687 B1 | 4/2002 | Joseph | |
| 6,461,467 B2 | 10/2002 | Blatchford | |
| 6,479,724 B1 | 11/2002 | Areskoug | |
| D468,548 S | 1/2003 | Head | |
| 7,520,872 B2 | 4/2009 | Biggie | |
| 7,731,702 B2 | 6/2010 | Bybordi | |
| 8,546,637 B2 * | 10/2013 | Holm | A61L 15/42 602/42 |
| 8,556,871 B2 | 10/2013 | Mormino | |
| 9,278,155 B2 | 3/2016 | Asmus | |
| 10,130,521 B2 * | 11/2018 | Junginger | A61F 13/00991 |
| 10,324,007 B2 * | 6/2019 | Thompson | G01N 1/2214 |
| 2002/0015726 A1 | 2/2002 | Scamilla Aledo | |
| 2003/0120229 A1 | 6/2003 | de Jong | |
| 2004/0247655 A1 | 12/2004 | Asmus | |
| 2008/0233348 A1 | 9/2008 | Ishiwatari | |
| 2009/0187130 A1 | 7/2009 | Asmus | |
| 2009/0216168 A1 * | 8/2009 | Eckstein | A61F 13/00063 602/43 |
| 2009/0299251 A1 | 12/2009 | Buan | |
| 2010/0159192 A1 | 6/2010 | Cotton | |
| 2012/0095380 A1 * | 4/2012 | Gergely | A61F 13/022 602/45 |
| 2012/0209226 A1 | 8/2012 | Simmons | |
| 2014/0024989 A1 * | 1/2014 | Ueda | A61F 13/0253 602/44 |
| 2014/0124232 A1 | 5/2014 | Sarchi | |
| 2014/0249495 A1 | 9/2014 | Mumby | |
| 2014/0350494 A1 | 11/2014 | Hartwell | |
| 2016/0120706 A1 | 5/2016 | Collinson | |
| 2017/0143552 A1 | 5/2017 | Hartwell | |

FOREIGN PATENT DOCUMENTS

| | | |
|---|---|---|
| EP | 2437803 | 4/2012 |
| EP | 2440260 | 4/2012 |
| GB | 2496310 | 5/2013 |
| WO | WO 1999-27975 | 6/1999 |
| WO | WO 2003-086493 | 10/2003 |
| WO | WO 2004-108854 | 12/2004 |
| WO | WO 2009-091682 | 7/2009 |
| WO | WO 2010-056541 | 5/2010 |
| WO | WO 2010-056543 | 5/2010 |
| WO | WO 2011-135284 | 11/2011 |
| WO | WO 2012-156655 | 11/2012 |
| WO | WO 2014-003957 | 1/2014 |
| WO | WO 2014-020440 | 2/2014 |
| WO | WO 2014-140608 | 9/2014 |
| WO | WO 2015-134249 | 9/2015 |
| WO | WO 2016-109420 | 7/2016 |

* cited by examiner

WOUND DRESSING WITH MULTIPLE ADHESIVE LAYERS

CROSS REFERENCE TO RELATED APPLICATIONS

This application is a national stage filing under 35 U.S.C. 371 of PCT/US2015/067655, filed Dec. 28, 2015, which claims the benefit of both U.S. Provisional Application No. 62/112,714, filed Feb. 6, 2015, and U.S. Provisional Application No. 62/098,058, filed Dec. 30, 2014, the disclosures of which are incorporated by reference in their entirety herein.

BACKGROUND

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.), BIOCLUSIVE™ (Johnson & Johnson Company, New Brunswick, N.J.), and OP-SITE™ (T.J. Smith & Nephew, Hull, England).

In addition, the length of time over which the medical dressings may remain in place over wounds may be limited by many factors. Among the factors that may limit the usable life of a medical dressing is the accumulation of fluids within the wound. Some medical dressings have included the use of negative pressure wound therapy in which fluids are removed from the beneath the wound dressings without requiring removal of the dressings from the patient. Dressings adapted for delivery of negative pressure wound therapy (such as those described in, e.g., U.S. Pat. Nos. 4,969,880; 5,261,893; 5,527,293; and 6,071,267 (all to Zamierowski)) often have constructions that can compromise the sterility of the wound over which they are placed. These effects can be compounded by wounds on or around irregular surfaces, such as the knee, elbow, shoulders, heel, and ankle.

Control of bacteria on the skin and in the wound are important factors for minimizing surgical site infections and improving healing of both acute and chronic wounds. However, high concentrations of some antimicrobial agents that effectively reduce bacteria on the skin are too toxic to the cells that are required for wound healing. Hence a dressing is needed that can effectively reduce bacteria on the skin and not harm cells required for wound healing.

SUMMARY

The present disclosure generally relates to wound dressings. A wound dressing of the present disclosure comprises a layer of porous material that is next to the wound, a layer of absorbent hydrophilic adhesive that extends over the porous layer and onto periwound skin, and a high moisture vapor transmission rate (hereinafter, "MVTR") adhesive/film backing. The absorbent hydrophilic adhesive retains excess wound exudate away from the wound and absorbs excess periwound moisture on the periwound skin. It is also a source of antimicrobial agent which help to mitigate bacteria on portions of the periwound skin immediately upon application of the dressing. However, the absorbent hydrophilic adhesive doesn't release significant levels of antimicrobial agent into the porous layer until exudate from the wound passes through the porous layer and to the absorbent adhesive. The absorbent hydrophilic adhesive also facilitates gentle securement and removal of the dressing.

The porous wound contact layer of the wound dressing of the present disclosure provides a structure to facilitate migration of wound exudate to the absorbent hydrophilic adhesive, and it further delays the onset of diffusion of the antimicrobial agent to the wound until the porous layer is sufficiently saturated with wound fluid. The porous wound contact layer also helps to minimize maceration of the wound and periwound skin by channeling moisture away from the skin to the absorbent hydrophilic adhesive. The high MVTR backing facilitates the evaporation of moisture from the absorbent hydrophilic adhesive so that the absorbent hydrophilic adhesive maintains its adhesive and sealing properties to skin along the perimeter of the porous wound contact layer.

In any embodiment, the porous wound contact layer can be an open cell foam with an adhesive-coated perforated film laminated thereto. The adhesive coating on the wound-facing side of the perforated film can be a hydrophobic soft silicone adhesive or a hydrophobic soft acrylate based adhesive which provides both gentle skin adhesive, and additional securement of the dressing to skin.

The present disclosure provides a wound dressing. The wound dressing can comprise a moisture-transmissible backing layer having a first major surface, a second major surface, and a backing layer perimeter; an absorbent hydrophilic adhesive adhered to at least a portion of the second major surface of the backing layer, the absorbent hydrophilic adhesive comprising an absorbent hydrophilic adhesive perimeter; an antimicrobial agent disposed in the absorbent hydrophilic adhesive; a porous layer having a first side adhered to the absorbent hydrophilic adhesive, a second side, and a porous layer perimeter; and a second hydrophobic adhesive adhered to the second side of the porous layer. 100% of the absorbent hydrophilic adhesive perimeter can be overlapped by the backing layer. At least 50% of the porous layer perimeter can be overlapped by the absorbent hydrophilic adhesive.

In any embodiment of the wound dressing, the absorbent hydrophilic adhesive can have a thickness of about 0.2 mm to about 4.0 mm. In any of the above embodiments, the absorbent hydrophilic adhesive can comprise less than 40% (w/w) water. In any of the above embodiments, the dressing further can comprise a perforated layer disposed between the second side of the porous layer and the second hydrophobic adhesive. In any of the above embodiments, the absorbent hydrophilic adhesive can have a shear modulus between about 5,000 pascals and about 50,000 pascals at 24° C. at a shear of 1 rad/sec. In any of the above embodiments, the absorbent hydrophilic adhesive can have a loss shear modulus between about 2,000 pascals and about 20,000 pascals at 24° C. at a shear of 1 rad/sec.

The terms "comprises" and variations thereof do not have a limiting meaning where these terms appear in the description and claims.

As used herein, "a," "an," "the," "at least one," and "one or more" are used interchangeably. Thus, for example, a porous layer can be interpreted to mean "one or more" porous layers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to a wound dressing that can be left on a wound site to manage fluid accumulation at a wound site for extended periods of time (e.g., up to 5 days, up to 7 days). In addition, the construction of the dressing (e.g., having an antimicrobial agent disposed in the absorbent hydrophilic adhesive and a porous layer disposed between the absorbent hydrophilic adhesive at the wound site) provides instantaneous, relatively-high concentrations of the antimicrobial agent at the periwound skin interface and it provides relatively lower concentrations of antimicrobial agent at the wound site. The materials from which the dressing is constructed provide a wound-contact surface that facilitates conformity of the wound dressing to anatomical structure.

Figure 1:
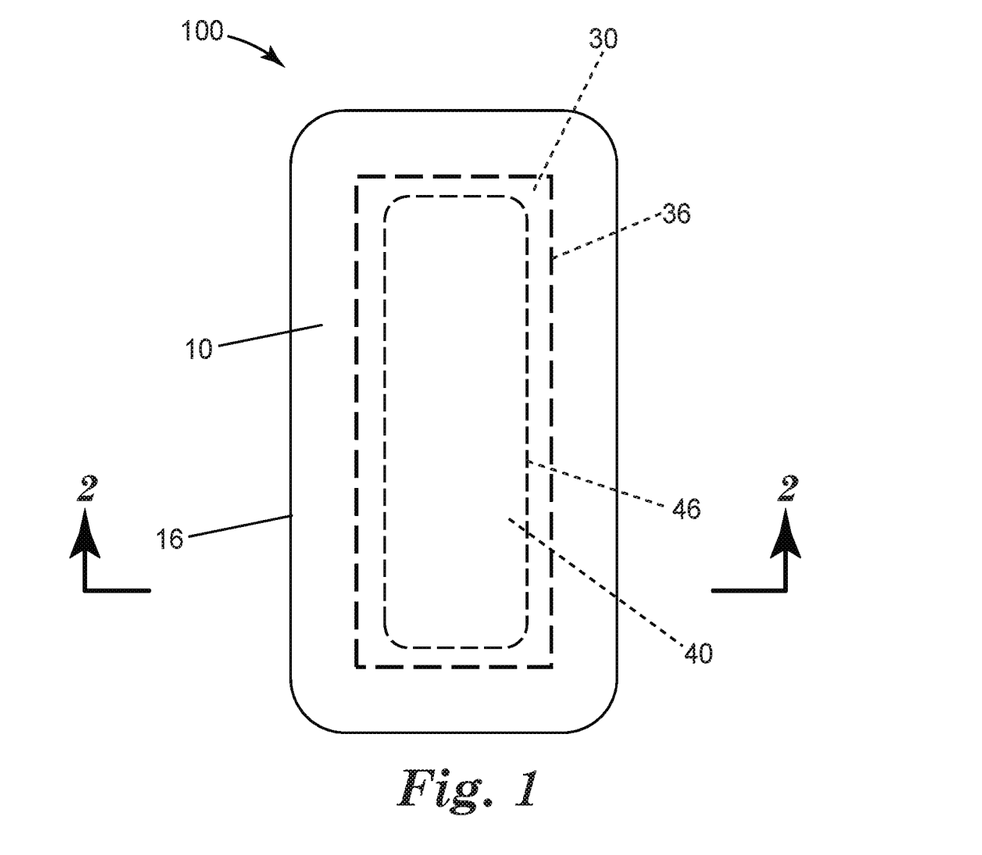
FIG. 1 is a schematic plan view of one embodiment of a wound dressing with an optional perforated layer according to the present disclosure.
Figure 2:
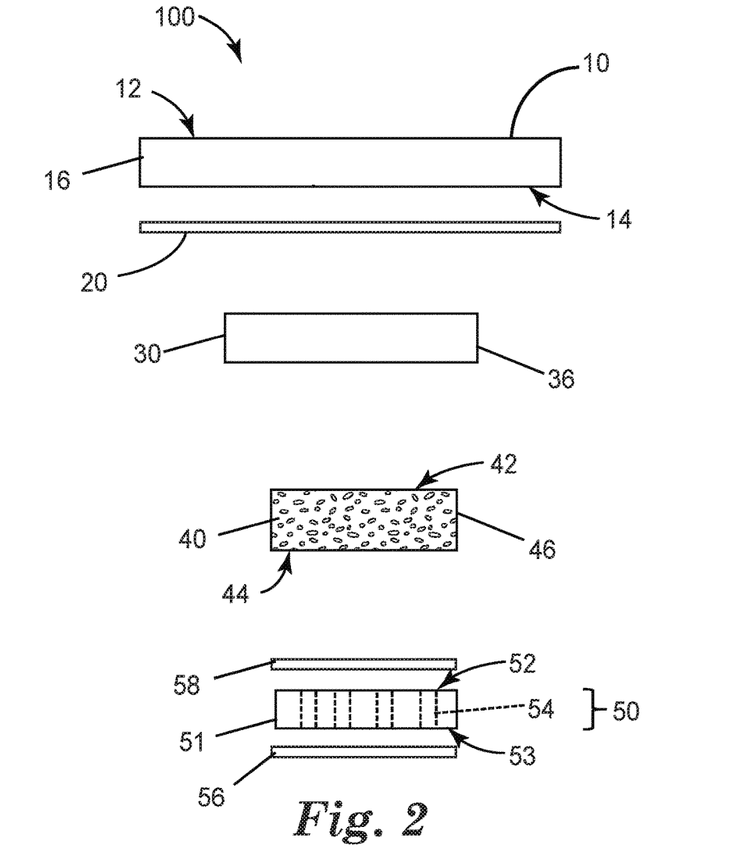
FIG. 2 is an exploded side view of the wound dressing of FIG. 1.
Figure 3:
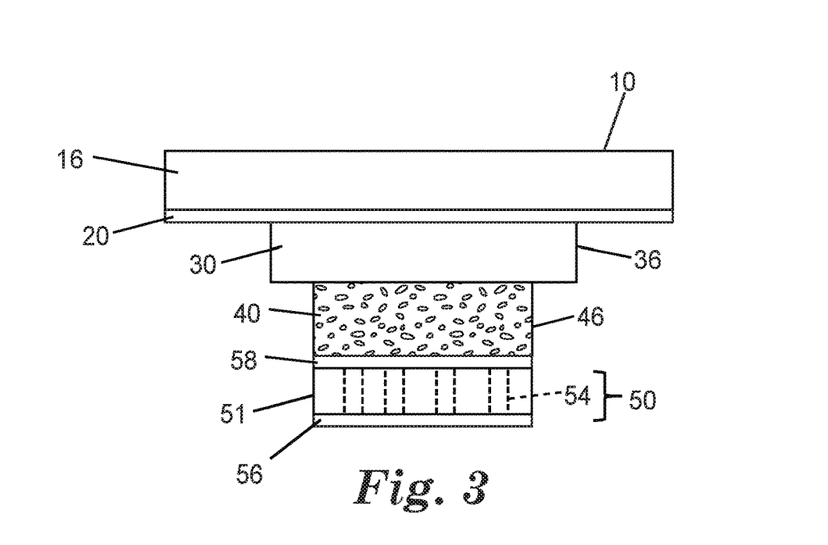
FIG. 3 is a side view of the wound dressing of FIG. 1.

Turning now to the drawings, FIG. 1 is a plan view, FIG. 2 is an exploded side view, and FIG. 3 is a side view of one embodiment of a wound dressing 100 according to the present disclosure. The dressing 100 comprises a backing layer 10, an absorbent hydrophilic adhesive 30 adhered to at least a portion of the moisture-transmissible backing layer 10, and a porous layer 40. In any embodiment, the dressing 100 optionally comprises a perforated layer 50. The wound dressing 100 can be formed in a variety of shapes including, for example, a circle, an oval, a trapezoid, a rectangle, and a square, which can include rounded corners for each of the various shapes.

The backing layer 10 has a first major surface 12, a second major surface 14 opposite the first major surface, and a backing layer perimeter 16 that defines the edge of the backing layer. The backing layer 10 is made from a flexible material (e.g., a polymeric elastic film, an elastic non-woven fabric, or combinations thereof) that is compliant enough to conform to the anatomical contours of skin surfaces. The backing layer perimeter 16 defines outer edges of the backing layer 10.

The backing layer 10 includes a liquid-impervious, moisture-vapor permeable polymeric film, although it can include a variety of other materials, which are preferably used in combination with a liquid-impervious, moisture-vapor permeable polymeric film. The liquid-impervious, moisture-vapor permeable polymeric film can be a conformable organic polymeric material. Herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture-vapor permeable polymeric films of the backing layer 10 can be of a wide range of thicknesses. Preferably, they are from about 10 microns or 12 microns to 75 microns or 250 microns thick. Furthermore, they can include one or more layers tailored to have the desired properties. These layers can be coextruded and/or bonded together with adhesive layers, for example, as long as the overall properties of the film and article, as described herein, are met. In any embodiment, the backing layer 10 has a thickness of about 15 μm to about 250 μm.

Examples of suitable materials for the liquid-impervious, moisture-vapor permeable polymeric films for backing layer 10 include synthetic organic polymers including, but not limited to: polyurethanes commercially available from Lubrizol, Wickliffe, Ohio, under the trade designation ESTANE, including ESTANE 58237 and ESTANE 80MVT; polyamide block copolymers commercially available from Elf Atochem, Philadelphia, Pa., under the trade designation PEBAX, including PEBAX MV1074; poly-ester block copolymers commercially available from DuPont, Wilmington, Del., under the trade designation HYTREL. The polymeric films can be made of one or more types of monomers (e.g., copolymers) or mixtures (e.g., blends) of polymers. An example material is thermoplastic polymers (e.g., those that soften when exposed to heat and return to their original condition when cooled), such as thermoplastic polyurethane.

Backing layer 10 of the wound dressings of the present invention can be other breathable materials including, for example, nonwoven, woven, and knit webs, porous films (e.g., provided by perforations or microporous structure), or other known backings. One such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.). Other suitable breathable backings are apertured films such as DELNET® films from DeltStar Technologies (Middletown, Del.).

Backing layer 10 may be a combination of a liquid-impervious, moisture-vapor permeable polymeric film and a moisture-vapor permeable nonwoven, woven, or knit web, or a porous film that can, among other advantages, impart enhanced structural integrity and improved aesthetics to the dressings. The layers within the backing are preferably bonded together using an adhesive layer, for example, that can be continuous or discontinuous (e.g., such as that produced with a pattern-coated adhesive layer), although other means of bonding can be used including thermomechanical bonding, such as thermal bonding or ultrasonic welding.

Adhered to (e.g., coated onto) at least a portion (e.g., a continuous portion that extends along the second major surface 14 proximate the entire backing layer perimeter 16) is a first adhesive 20. In use, the first adhesive 20 forms a seal (e.g., a liquid seal around the entire backing layer perimeter 16) between the backing layer 10 and the skin to which the dressing is applied.

Preferably, the backing layer/first adhesive composite should permit transmission of moisture vapor therethrough at a rate equal to or greater than human skin. Preferably, the uncoated film (i.e., the backing layer without the first adhesive coated thereon) transmits moisture vapor therethrough at a rate of at least 10 g/10 cm$^2$/24 hrs. as measured by EN-13726-1:2002 Section 3.3. Even more preferably, the uncoated backing layer transmits moisture greater than 20 g/10 cm$^2$/24 hours. In any embodiment, the adhesive coated portions of the backing layer transmit moisture vapor at rate of at least 0.8 g/10 cm$^2$/24 hours, and preferably greater than 1.6 g/10 cm$^2$/24 hours.

The backing layer 10 is preferably conformable to anatomical surfaces. As such, when the backing layer is applied to an anatomical surface, it conforms to the surface even when the surface is moved. The preferred backing layer 10 is also conformable to animal anatomical joints. When the joint is flexed and then returned to its unflexed position, the backing layer stretches to accommodate the flexion of the joint, but is resilient enough to continue to conform to the joint when the joint is returned to its unflexed condition. Preferably, the backing layer has an ultimate elongation of greater than 200%. More preferably, the backing layer has an ultimate elongation of greater than 400%.

A description of this characteristic of backing layers preferred for use with the wound dressing of the present disclosure can be found in issued U.S. Pat. Nos. 5,088,483 and 5,160,315, the disclosures of which are hereby incorporated by reference in their entirety. Particularly preferred backing layers are elastomeric polyurethane, co-polyester, or polyether block amide films. These films combine the desirable properties of resiliency, high moisture vapor permeability, and transparency found in preferred backing layers.

The first adhesive typically is a pressure sensitive adhesive, and particularly an adhesive that can be applied to skin such as the acrylate copolymers described in U.S. Pat. No. RE 24,906, the disclosure of which is hereby incorporated by reference in its entirety; particularly a 97:3 iso-octyl acrylate:acrylamide copolymer. Another suitable first adhesive is a 70:15:15 isooctyl acrylate: ethyleneoxide acrylate: acrylic acid terpolymer, as described in U.S. Pat. No. 4,737,410 (Example 31), the disclosure of which is hereby incorporated by reference. Other useful first adhesives are described in U.S. Pat. Nos. 3,389,827, 4,112,213, 4,310,509, and 4,323,557, the disclosures of which are hereby incorporated by reference in their entireties.

Inclusion of medicaments or antimicrobial agents in the first adhesive is also contemplated, as described in U.S. Pat. Nos. 4,310,509 and 4,323,557 both of which are hereby incorporated by reference in their entireties. Silicone or polyurethane adhesive can also be used. Suitable silicone adhesives are disclosed in PCT Publication Nos. WO2010/056541 and WO2010/056543, the disclosures of which are herein incorporate by reference. Other suitable silicone adhesive elastomers are disclosed in U.S. Pat. No. 6,479,724.

According to the present disclosure, typically the first adhesive on the backing is discontinuous in order to achieve a high moisture vapor transmission rate through the adhesive/backing layers. A discontinuous adhesive can be achieved via either pattern coating as described in U.S. Pat. No. 4,595,001 and U.S. Patent Application Publication No. 2008-0233348, or via a converting step where holes or a large hole is cut out of the adhesive and laminated to the backing. The first adhesive-coated backing layer is able to transmit moisture vapor at a rate greater to or equal to that of human skin. Other ways of achieve a high moisture vapor transmission rate of a continuous adhesive coating are described in U.S. Pat. No. 8,546,637; which is incorporated herein by reference in its entirety.

The preferred pressure sensitive adhesives for first adhesive 20 described above preferably transmit moisture vapor at rate greater to or equal to that of human skin. While such a characteristic can be achieved through the selection of an appropriate adhesive or through use of a nonwoven (e.g., melt blown) adhesive (as described in U.S. Pat. Nos. 6,171,985, 6,368,687, and PCT Publication No. WO 99/27975 (all of which are incorporated herein by reference in their entirety)), it is also contemplated in the wound dressings of the present disclosure that other methods of achieving a high relative rate of moisture vapor transmission may be used, such as pattern coating (not shown) the first adhesive on the backing layer. In addition, this adhesive has low absorbency (i.e., less than 15% its dry weight, and preferably less than 5% its dry weight) when submerged in isotonic saline at 37 Celsius for 24 hours.

The absorbent hydrophilic adhesive 30 is adhered to at least a portion of the second major surface 14 of the backing layer 10. The absorbent hydrophilic adhesive 30 comprises an absorbent hydrophilic adhesive perimeter 36 that defines the outer edge of the absorbent hydrophilic adhesive. The absorbent hydrophilic adhesive perimeter 36 is spaced apart from the backing layer perimeter 16. Thus, in use, when the first adhesive 20 of the backing layer 10 is applied to a treatment surface (not shown), the backing layer 10 overlaps 100 percent of the absorbent hydrophilic adhesive perimeter 36. As used herein, a first piece (e.g. the backing layer) can be said to "overlap" or "overlie" a second piece (e.g., the absorbent hydrophilic adhesive) if it covers a portion of either the second piece, or a portion of some third piece that is covered along its opposite side by the second piece. In other words, one piece can "overlap" or "overlie" another piece even though separated by a third piece.

The absorbent hydrophilic adhesive 30 can be relatively thin. In any embodiment, the absorbent hydrophilic adhesive has a thickness of about 0.2 mm to about 4.0 mm. In any embodiment, the absorbent hydrophilic adhesive has a thickness of about 0.4 mm to about 3 mm. Preferably, the thickness of the absorbent hydrophilic adhesive 30 is greater than 0.50 mm, and more preferably greater than 1.0 mm. The absorbent hydrophilic adhesive 30 contains less than 45% water (w/w) and preferably less than 25% water. It can absorb at least 1.0 times its dry weight when exposed to isotonic saline for 24 hours at 37 Celsius. The absorbent hydrophilic adhesive 30 should also be soft, and have high integrity when dry. The absorbent hydrophilic adhesive 30 will swell when it absorbs moisture, but it is not soluble in water or isotonic saline. An example of a useful absorbent hydrophilic adhesive is the gel adhesive described in U.S. Patent Application Publication No. 2009/0187130. Preferably, the absorbent hydrophilic adhesive layer should adhere to and extend over the porous layer, and at it should extend outside of 70% of the perimeter of the porous layer.

The absorbent hydrophilic adhesive 30 is capable of absorbing and retaining an aqueous liquid having an ionic strength similar to blood. Thus, this property can be tested easily by quantifying the absorbance of physiological saline. In any embodiment, the absorbent hydrophilic adhesive is capable of absorbing at least 0.4 times its dry weight; preferably, at least 1.0 times its dry weight; more preferably, greater than or equal to 1.5 times its dry weight; even more preferably, greater than or equal to 4 times its dry weight when contacted with an isotonic saline solution at 37° C. for 24 hours. The absorbent hydrophilic adhesive also has high moisture retention in that it will retain greater than 50% of what it absorbs (i.e., residual absorbent capacity) when externally compressed with 40 mm Hg pressure.

In any embodiment, the absorbent hydrophilic adhesive 30 can include polyglycerol-3, crosslinked polyvinylpyrrolidone, and/or hydroxypropyl guar. Nonlimiting examples of suitable absorbent hydrophilic adhesives and methods of making said absorbent hydrophilic adhesives are described in International Publication No. WO 2009/091682, which hereby is incorporated by reference in its entirety. The absorbent hydrophilic adhesive comprises an antimicrobial agent such as, for example an antimicrobial biguanide (e.g., chlorhexidine gluconate).

Suitable absorbent hydrophilic adhesive compositions include, for example, a natural hydrogel, such as pectin, gelatin, or carboxymethylcellulose (CMC) (Aqualon Corp., Wilmington, Del.), a semi-synthetic hydrogel, such as crosslinked carboxymethylcellulose X4ink CMC) (e.g. Ac-Di-Sol; FMC Corp., Philadelphia, Pa.), a synthetic hydrogel, such as cross linked polyacrylic acid (PAA) (e.g., CARBOPOL™ No. 974P; B.F. Goodrich, Brecksville, Ohio), or a combination thereof.

In most embodiments, the absorbent hydrophilic adhesive comprises a swellable, crosslinked poly(N-vinyl lactam), a swelling agent and a modifying polymer present in an amount sufficient to form a cohesive, pressure-sensitive adhesive composition as described further in International Publication No. WO 2004/108854, which is incorporated herein by reference in its entirety. The amount of swelling agent to be mixed with the crosslinked swellable poly(N-vinyl lactam) can range from about 50 to about 90 weight percent of the composition. Consequently, exclusive of any biocompatible and/or therapeutic and/or ionically conductive materials to be added to the composition, the weight percent of the swellable poly(N-vinyl lactam) can be from about 10 to about 50 weight percent. When the poly(N-vinyl lactam) is poly(N-vinyl pyrrolidone), the weight percent of poly(N-vinyl pyrrolidone) can range from about 15 to about 45 percent. In particular embodiments, the poly (N-vinyl pyrrolidone) can range from about 18 percent to about 35 percent.

In most embodiments, the absorbent hydrophilic adhesive composition of the present invention comprises a swellable, poly(N-vinyl lactam) that is radiation-crosslinked, typically while the lactam is in a solid form. In other embodiments, the poly (N-vinyl) lactam is crosslinked by free-radical polymerization, either in bulk or in solution, of a precursor containing an N-vinyl lactam monomer, optionally other monomers, and a crosslinking compound as described in U.S. Pat. No. 4,931,282, which is incorporated herein by reference in its entirety. Poly(N-vinyl lactam) useful in an absorbent hydrophilic adhesive of present disclosure can be provided in any form susceptible to being crosslinked such as the solid forms described in U.S. Pat. Nos., 4,931,282; 5,225,473; and 5,389,376; which are incorporated herein by reference in their entirety. Typically, the poly(N-vinyl lactam) is a homopolymer of N-vinyl-2-pyrrolidone.

After exposure to ionizing radiation, poly(N-vinyl lactam) can have a swelling capacity in water of at least about 15, typically at least about 30, and often at least about 40 as described in U.S. Pat. No. 5,409,966, which is incorporated herein by reference in its entirety. Poly(N-vinyl lactam) in any solid form may be crosslinked for use when subjected to ionizing radiation from a high-energy source.

The modifying polymer is present in the absorbent hydrophilic adhesive composition to maintain and/or increase cohesiveness while reducing adhesiveness. When added with the swelling agent, the modifying polymer becomes solubilized or suspended in the swelling agent. Typically, the modifying polymer will form a viscous solution or viscous hydrogel when combined with the swelling agent in a ratio of modifying polymer to swelling agent of 1:9.

The choice of swelling agent typically will determine the appropriate modifying polymer to accomplish a reduction in adhesion while maintaining or improving cohesion of the adhesive composition. Modifying polymers that are poorly solubilized in one swelling agent may be highly swollen in a different swelling agent for use in the present invention. In some embodiments, examples of suitable modifying swellable polymers include, but are not limited to, polysaccharides, polysaccharide derivatives, acrylates, acrylate derivatives, cellulose, cellulose derivatives, and combinations thereof.

In particular embodiments, modifying swellable polymers for use in the present invention are hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

The amount of modifying polymer can range up to about 50 weight percent of the composition. Consequently, exclusive of any biocompatible and/or therapeutic and/or ionically-conductive materials to be added to the composition, the weight percent of the modifying polymer can be from about 0.1 to about 40 weight percent. When the modifying polymer is hydroxypropyl guar, the weight percent of hydroxypropyl guar can range from about 1 to about 20 percent.

The absorbent hydrophilic adhesive composition also comprises a swelling agent that can swell both the crosslinked poly(N-vinyl lactam) polymer and the modifying polymer, and which is biocompatible with human skin. Nonlimiting examples of swelling agents useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol swelling agents which do not cause skin irritation or toxic reaction, and water.

Depending on the ultimate use desired for the absorbent hydrophilic adhesive composition, non-volatile and/or volatile swelling agents may be used. One suitable swelling agent may comprise volatile swelling agent and non-volatile swelling agent, such as a mixture of glycerin or polyethylene glycol with water. In some embodiments, non-volatile swelling agents may be used by themselves such as, for example, glycerin or polyethylene glycol. Likewise, volatile swelling agents such as water may be used by themselves in the compositions of the invention. For this disclosure, "essentially non-volatile" means that a swelling agent as used in the present disclosure will render the adhesive polymer, such as radiated poly(N-vinyl lactam), sufficiently cohesive and pressure sensitive adhesive, such that less than ten percent (10%) of a given volume of nonvolatile swelling agent evaporates after exposure to processing or storage conditions.

The swelling agent can be added in an amount ranging from about 50 to about 90 weight percent of the absorbent hydrophilic adhesive composition and preferably from about 60 to about 80 weight percent. In some embodiments, glycerin and polyethylene glycol are chosen to be the essentially non-volatile swelling agent. Both glycerin and polyethylene glycol can comprise up to 100 weight percent of the swelling agent.

The absorbent hydrophilic adhesive 30 is useful for containing a number of substances, optionally including antimicrobial agents, drugs for transdermal drug delivery, chemical indicators to monitor hormones or other substances in a patient, etc.

The absorbent hydrophilic adhesive can facilitate the delivery of an antimicrobial agent to the skin, reducing the likeliness of an infection to a percutaneous device or to treat infections of the skin or wounds. In most embodiments, the antimicrobial agent is added to the absorbent hydrophilic adhesive in levels up to 10% by weight of the total composition.

There are numerous biologically active materials, including antimicrobial agents that can be disposed in the absorbent hydrophilic adhesive. Examples of antimicrobial agents include parachlorometaxylenol; triclosan; chlorhexidine and its salts such as chlorhexidine gluconate, polyhexamethylene biguanide and its salts such as poly hexamethylene biguanidine chloride, iodine, idodophors, fatty acid monoesters; poly-n-vinyl pyrrolidone-iodophors; silver oxide, silver and its salts, peroxides (e.g. hydrogen peroxide), antibiotics (e.g. neomycin, bacitracin, and polymyxin B). Other suitable antimicrobial agents are those listed in International Publication No. WO 2004/108854.

A method of preparing an absorbent hydrophilic adhesive composition of the present disclosure comprises mixing crosslinked poly(N-vinyl lactam) with a swelling agent and a modifying polymer, and other additives in a solvent which is or may be somewhat volatile at or above ambient temperatures. Typically, the swelling agent, modifying polymer, and other additives, such as antimicrobial agents, are in essentially unirradiated form. Examples of suitable volatile solvents include water, ethanol, methanol, and isopropanol. A quantity of the resulting suspension is then cast onto a surface of a substrate, such as a release liner or a backing material and then stored. The volatile solvent is evaporated by heating such as by the application of microwave energy, infrared energy, or by convective air flow or the like, in order to form a cohesive, pressure-sensitive adhesive composition on the substrate. Often, a drying oven heated to about 65 degree C. may be employed for the evaporation step. A product release liner can optionally be laminated over the exposed surface of the composition to protect it from contamination.

In any embodiment, the absorbent hydrophilic adhesive 30 can comprise a hydrocolloid that contains polyisobutylene, a polyisoprene based polymer, a soluble absorbent, an insoluble absorbent, and a tackifier. Suitable hydrocolloid compositions include, for example, 20-40% by weight of polyisobutylene (e.g., OPPANOL® polyisobutylene from BASF, Florham Park, N.J.), 15-40% of a polyisprene based polymer, and a 15-45% by soluble and insoluble absorbents such as carboxymethylcellulose (CMC) (Aqualon Corp., Wilmington, Del.) and cross-linked carboxymethylcellulose X4ink CMC) (e.g. Ac-Di-Solt CMC; FMC Corp., Philadelphia, Pa.), respectively, and less than 15% by weight of a tackifier such as WINGTACK® 95 resin (Sartomer Co., Exton, Pa.).

In some embodiments, the hydrocolloid comprises a crosslinked hydrophobic silicone gel with soluble and/or insoluble absorbents dispersed therein. The absorbent content should be 15-45% by weight.

In addition to being capable of absorbing aqueous liquid, the absorbent hydrophilic adhesive 30 of the present disclosure, when adhered to the backing layer 10, is moisture transmissive. Thus, in any embodiment, the backing layer 10 with the absorbent hydrophilic adhesive 30 adhered thereto has a Moisture Vapor Transmission Rate (MVTR)≥1 g/10 $cm^2$/24 hours, as measured by EN-13726-1:2002 Section 3.3. Preferably, this Moisture Vapor Transmission Rate is greater than 3 g/10 $cm^2$/24 hours. Advantageously, because the wound dressing 100 has a moisture vapor-transmissive backing layer and a moisture vapor-transmissive absorbent hydrophilic adhesive, moisture can be transported away from the wound site and out of the dressing 100 by passing through the absorbent hydrophilic adhesive and out of the intact backing layer (in the vapor state). A high moisture vapor transmission rate through the absorbent hydrophilic adhesive and backing layer is important because it permits the management of relatively large quantities of wound exudate.

In any embodiment, before applying the wound dressing of the present disclosure to a treatment site, the absorbent hydrophilic adhesive comprises less than 40% (w/w) water. In any embodiment, before applying the wound dressing of the present disclosure to a treatment site, the absorbent hydrophilic adhesive comprises less than 25% (w/w) water. Preferably, before applying the wound dressing of the present disclosure to a treatment site, the absorbent hydrophilic adhesive comprises less than 10% (w/w) water. The use of an absorbent hydrophilic adhesive comprising <40% (w/w) water, <25% (w/w) water, or <10% (w/w) reduces the need for specialized packaging that would otherwise be needed to preserve the water in the absorbent hydrophilic adhesive during storage before use.

The elastic properties (e.g., as indicated by the storage modulus (G')) of the absorbent hydrophilic adhesive is selected so that, within the range of thicknesses of the absorbent hydrophilic adhesive, the wound dressing is conformable, yet of high integrity so that it won't readily fall apart when stretched. In any embodiment, before applying the wound dressing of the present disclosure to a treatment site, the absorbent hydrophilic adhesive has a storage shear modulus between about 5,000 pascals and about 50,000 pascals at 24° C. at a shear rate of 1 rad/sec. Preferably between 10,000 pascals and about 30,000 pascals.

In addition, the loss modulus (G") indicates the viscous response of the absorbent hydrophilic adhesive 30. In any embodiment, before applying the wound dressing of the present disclosure to a treatment site, the absorbent hydrophilic adhesive has a loss shear modulus between about 2,000 pascals and about 20,000 pascals (inclusive) at 24° C. at a shear of 1 rad/sec. Preferably, the loss modulus G" is between about 3,000 pascals and about 15,000 pascals, inclusive. Advantageously, an absorbent hydrophilic adhesive having a loss modulus G" between about 2,000 pascals and about 20,000 pascals (inclusive) at 24° C. at a shear of 1 rad/sec is sufficiently soft to create a good seal on skin but not so soft that flows readily and easily loses its integrity.

Returning to the drawings, a wound dressing 100 according to the present disclosure comprises a porous layer 40. The porous layer 40 has a first side 42, a second side 44, and a porous layer perimeter 46 that defines the outer edge of the porous layer, which further defines a porous layer area. The first side 42 of the porous layer 40 is adhered to the absorbent hydrophilic adhesive 30.

In any embodiment, at least 50% of the porous layer perimeter 46 is overlapped by the absorbent hydrophilic adhesive 30. In any embodiment, more than 50% of the porous layer perimeter 46 is overlapped by the absorbent hydrophilic adhesive 30. In any embodiment, at least 60% of the porous layer perimeter 46 is overlapped by the absorbent hydrophilic adhesive 30. In any embodiment, at least 70% of the porous layer perimeter 46 is overlapped by the absorbent hydrophilic adhesive 30. In any embodiment, at least 75% of the porous layer perimeter 46 is overlapped by the absorbent hydrophilic adhesive 30. In any embodiment, at least 80% of the porous layer perimeter 46 is overlapped by the absorbent hydrophilic adhesive 30. In any embodiment, at least 85% of the porous layer perimeter 46 is overlapped by the absorbent hydrophilic adhesive 30. In any embodiment, at least 90% of the porous layer perimeter 46 is overlapped by the absorbent hydrophilic adhesive 30. In any embodiment, at least 95% of the porous layer perimeter 46 is overlapped by the absorbent hydrophilic adhesive 30. In any embodiment, 100% of the porous layer perimeter 46 is overlapped by the absorbent hydrophilic adhesive 30. Preferably, the absorbent hydrophilic adhesive 30 extends past the porous layer perimeter 46 (i.e., toward the backing layer perimeter 16) by at least 3 mm and more preferably at least 5 mm.

In addition to providing a good seal to skin, the absorbent hydrophilic adhesive 30 also acts as a reservoir for fluid such that it will take up moisture from the porous layer which prevents the porous layer from becoming saturated with liquid. Less liquid in the porous layer may result in less maceration of the skin proximate the wound site.

The absorbent hydrophilic adhesive composition can deliver an antimicrobial agent to the skin, reducing the likeliness of an infection to a percutaneous device or to treat infections of the skin or wounds. In most embodiments, the antimicrobial agent is added in levels up to 10% by weight of the total composition.

There are numerous biologically active materials, which include antimicrobial agents. Examples of antimicrobial agents include parachlorometaxylenol; triclosan; chlorhexidine and its salts such as chlorhexidine gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymyxin B). Other suitable antimicrobial agents are those listed in International Publication No. WO 2004/108854.

The porous layer 40 is configured to facilitate passage of fluid (e.g., blood or other fluids leaking from a wound site such as an incisional wound, for example) through the porous layer to the absorbent hydrophilic adhesive 30. In any embodiment, the porous layer 40 can comprise open-cell foam, a woven fabric (e.g., gauze), or a nonwoven fabric. Multi-layer porous polymer films would also be acceptable.

An additional purpose of the porous layer 40 is to increase the diffusion pathway for the antimicrobial to diffuse from the absorbent hydrophilic adhesive to an open wound, and therefore reduce the concentration of antimicrobial agent that can reach the wound surface. The porous layer 40 is preferably comprised of an open cell foam, non-woven, or woven material. It could also be perforated or microporous film porous film. For an open cell foam, it should have a density of less than 0.2 g/cm$^2$, and a thickness of less than 8 mm. For a woven or non-woven, the basis weight of the non-woven or woven material should be less than 500 g/m$^2$. The porous layer 40 can be comprised of different layers such as a porous film laminated to a non-woven.

In any embodiment, the porous layer 40 can be combination of layers of material. For example, a non-woven fabric laminated (or otherwise attached) to a foam could be considered the porous layer. In a preferred embodiment, a non-woven fabric with a porous film (macroporous or microporous) laminated to one or both sides of it, that is then laminated to an open cell foam can function as a good porous layer because the multiple layers enables fluid to readily pass through the porous layer.

In any embodiment, a wound dressing according to the present disclosure further can comprise a second hydrophobic adhesive (e.g., comprising a soft silicone gel adhesive or a soft acrylate gel adhesive as described in International Publication No. WO 2015/134249, which is incorporated herein by reference in its entirety) that is directly attached to the second side of the porous layer. Optionally, a perforated layer can be disposed between the second side of the porous layer and the second hydrophobic adhesive. The perforated layer can comprise perforated film with the second hydrophobic adhesive on the wound-facing side of the perforated film and an acrylate adhesive on the side that faces the porous layer 40. A non-limiting example of this type of perforated film is described in U.S. Patent Application Publication No. 2010/0159192, which is incorporated herein by reference in its entirety.

In any embodiment, a wound dressing 100 of the present disclosure optionally comprises a perforated layer 50. The perforated layer 50 comprises a substrate 51 (e.g., a polymeric film substrate, a foam, a non-woven fabric, a woven fabric, or a combination of any two or more of the foregoing materials) with a first surface 52, a second surface 53, and a plurality of perforations 54 extending therethrough. The perforations 54 provide a liquid pathway for exudate from the wound to pass through the substrate 51 and into the porous layer 40.

The first surface 52 of the perforated layer 50 is adhered to the second side 44 of the porous layer 40 via a perforated layer attachment adhesive 58, which may be coated onto the perforated layer 50. The second adhesive may be any suitable adhesive for adhering the perforated layer 50 to the porous layer 40. Optionally, the perforated layer 50 may comprise a second hydrophobic adhesive 56 coated thereon. The second hydrophobic adhesive 56 can provide additional securement of the wound dressing 100 to the treatment site (skin). In any embodiment, the second hydrophobic adhesive 56 can comprise a hydrophobic soft silicone adhesive or a soft acrylate gel adhesive. The perforated layer attachment adhesive 58 and second hydrophobic adhesive 56 can be coated onto the perforated layer 50 prior to perforating the substrate and, thus, the second and third adhesive also comprise perforations. Alternatively or additionally, the perforated layer attachment adhesive 58 and second hydrophobic adhesive 56 can be pattern coated onto the substrate 51. Advantageously, the perforations 54 in the perforated layer 50 not only provide a pathway for moisture transmission to the porous layer 40, they also render the perforated layer 50 highly conformable to the anatomical surfaces of various wound sites. The perforated layer does not have to be coextensive with the perimeter of porous layer.

Preferably the second hydrophobic adhesive 56 is a soft silicone gel adhesive or a soft acrylate gel adhesive and is greater than 50 microns thick; more preferably, greater than 75 microns thick. The second hydrophobic adhesive 56 provides added securement of the wound dressing to the tissue and periwound skin. It also keeps liquid off the periwound skin so it helps to minimize periwound skin maceration. Preferably, the adhesion to steel of this porous layer with a soft silicone adhesive layer is less than the adhesion to steel of the absorbent hydrophilic adhesive and/or the adhesive layer coated on the backing. In addition, the third adhesive has low absorbency in isotonic saline at 37 Celsius for 24 hours. (i.e., less than 15% of its dry weight, and preferably less than 5% its dry weight).

Figure 4A:
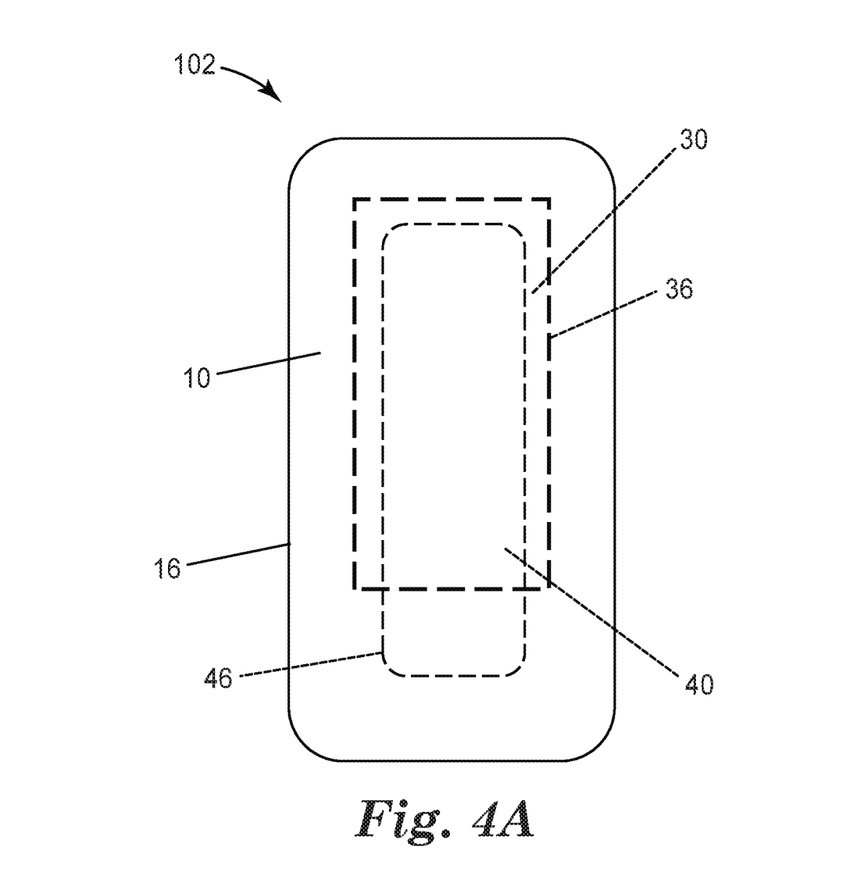
FIGS. 4A and 4B are schematic plan views of an alternative embodiments of a wound dressing according to the present disclosure, wherein the absorbent hydrophilic adhesive perimeter does not overlap 100% of the porous layer perimeter.
Figure 4B:
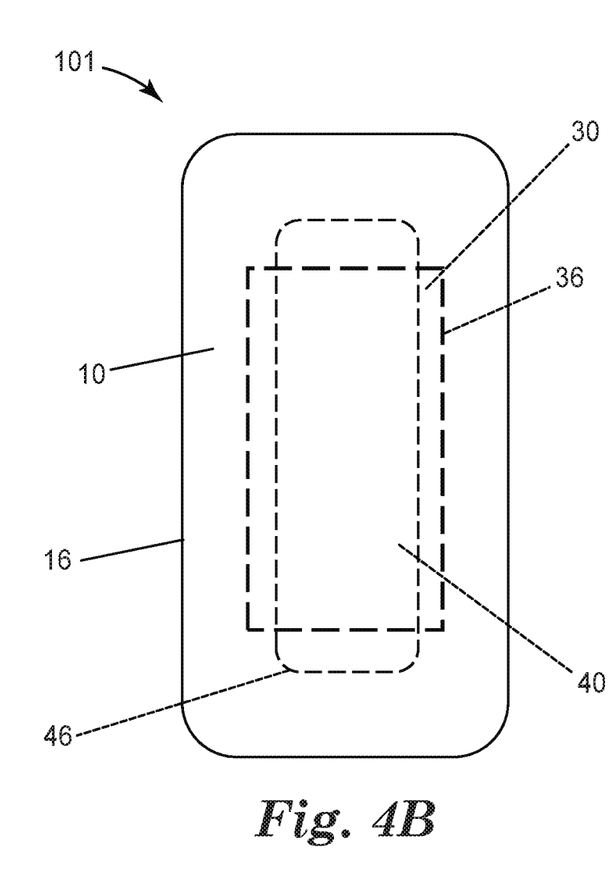

Although the illustrated embodiment of FIGS. 1 and 2 show a wound dressing 100 wherein the absorbent hydrophilic adhesive perimeter 36 completely overlaps the porous layer perimeter 46, it is contemplated that, in certain embodiments, the absorbent hydrophilic adhesive perimeter 36 does not overlap 100% of the porous layer perimeter 46, as discussed above. FIGS. 4A and 4B show two alternative embodiments of a wound dressing (wound dressing 102 and wound dressing 101, respectively) wherein the absorbent hydrophilic adhesive perimeter 36 of the absorbent hydrophilic adhesive 30 does not completely overlap the porous layer perimeter 46 of the porous layer 40. In these embodiments, the backing layer perimeter 16 of the backing layer 10 completely overlaps both the absorbent hydrophilic adhesive perimeter 36 and the porous layer perimeter 46.

In use, the wound dressing is applied to a treatment site with the adhesive side (i.e., of the second major surface) of the backing layer facing the skin.

Exemplary Embodiments

Embodiment A is a wound dressing, comprising:
a moisture-transmissible backing layer having a first major surface, a second major surface, and a backing layer perimeter;
wherein the second major surface has a first hydrophobic adhesive disposed thereon proximate the backing layer perimeter;
an absorbent hydrophilic adhesive adhered to at least a portion of the second major surface of the backing layer, the absorbent hydrophilic adhesive comprising an absorbent hydrophilic adhesive perimeter;
an antimicrobial agent disposed in the absorbent hydrophilic adhesive;
a porous layer having a first side adhered to the absorbent hydrophilic adhesive, a second side, and a porous layer perimeter; and
a second hydrophobic adhesive adhered to the second side of the porous layer;
wherein 100% of the absorbent hydrophilic adhesive 1 perimeter is overlapped by the backing layer;
wherein at least 50% of the porous layer perimeter is overlapped by the absorbent hydrophilic adhesive.

Embodiment B is the wound dressing of Embodiment A, wherein the absorbent hydrophilic adhesive has a thickness of about 0.2 mm to about 4.0 mm.

Embodiment C is the wound dressing of Embodiment A or Embodiment B, wherein the absorbent hydrophilic adhesive comprises less than 40% (w/w) water.

Embodiment D is the wound dressing of Embodiment C, wherein the absorbent hydrophilic adhesive comprises less than 25% (w/w) water.

Embodiment E is the wound dressing of any one of the preceding Embodiments, wherein the dressing further comprises a perforated layer disposed between the second side of the porous layer and the second hydrophobic adhesive.

Embodiment F is the wound dressing of Embodiment E, wherein the perforated layer comprises a perforated polymeric substrate.

Embodiment G is the wound dressing of any one of the preceding Embodiments, wherein adhesion to steel of the absorbent hydrophilic adhesive adhered to the backing layer is greater than adhesion to steel of the second hydrophobic adhesive adhered to the porous layer.

Embodiment H is the wound dressing of any one of the preceding Embodiments, wherein adhesion to steel of the absorbent hydrophilic adhesive adhered to the backing layer is greater than adhesion to steel is greater than adhesion to steel of the first hydrophobic adhesive adhered to the backing layer.

Embodiment I is the wound dressing of any one of the preceding Embodiments, wherein the backing layer comprises a polymeric elastic film, an elastic non-woven fabric, or combinations thereof.

Embodiment J is the wound dressing of Embodiment I, wherein the backing layer is about 15 µm to about 250 µm thick.

Embodiment K is the wound dressing of any one of the preceding Embodiments, wherein the backing layer has a Moisture Vapor Transmission Rate ≥10 g/10 $cm^2$/24 hours, as measured by EN-13726-1:2002 Section 3.3.

Embodiment L is the wound dressing of any one of the preceding Embodiments, wherein the backing layer with the absorbent hydrophilic adhesive adhered thereto has a Moisture Vapor Transmission Rate ≤1 g/10 $cm^2$/24 hours, as measured by EN-13726-1:2002 Section 3.3.

Embodiment M is the wound dressing of any one of the preceding Embodiments, wherein the absorbent hydrophilic adhesive has a shear modulus between about 5,000 pascals and about 50,000 pascals at 24° C. at a shear of 1 rad/sec.

Embodiment N is the wound dressing of any one of the preceding Embodiments, wherein the absorbent hydrophilic adhesive has a loss shear modulus between about 2,000 pascals and about 20,000 pascals at 24° C. at a shear of 1 rad/sec.

Embodiment O is the wound dressing of any one of the preceding Embodiments, wherein the porous absorbent layer comprises open-cell foam, a woven fabric, a nonwoven fabric, porous films, or a combination thereof.

Embodiment P is the wound dressing of any one of the preceding Embodiments, wherein the absorbent hydrophilic adhesive is capable of absorbing ≥1.5 times its dry weight when contacted with an isotonic saline solution at 37° C. for 24 hours.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Adhesion to Steel Test.

The adhesion to steel test was conducted using 304 AISI stainless steel plates with a bright annealed finish. Dimensions of the plates were 51 mm×127 mm×1.6 mm. The test surfaces was cleaned prior to each test one time using a disposable laboratory wipe saturated with isopropanol and three times with a disposable laboratory wipe saturated with n-heptane. The surface was allowed to dry prior to placing the sample on the test surface. The length of the test sample was 1" wide. Prior to measuring the adhesive force, the adhesive side of the sample was manually pressed against the steel plate and the nonadhesive side of the sample was rolled with a roller once in each direction to press the adhesive side against the plate. The roller had a total diameter of 3.75" (95 mm), a face width of 1.75" (44 mm), and it was covered with approximately 0.25" (6 mm) thickness of 75-85 durometer hardness rubber having an effective rolling weight of 4.5 pounds or 2043 grams. The rolling speed was approximately 50 mm/second. The sample was tested immediately after rolling using a 180 degree peel at a rate of 305 mm/min. Testing was conducted in a room at 25 Celsius and 50% relative humidity.

Example 1

Preparation of a Backing Layer with a Hydrophobic Adhesive Coated on One Side

A 23 micron thick film of Estane® 58237 thermoplastic polyurethane (Lubrizol Corporation, Wickliffe, Ohio) was used as the backing layer. The film was laminated to a discontinuous (pattern of approximately 1 mm diameter holes with 10% total open area) acrylate adhesive layer with coating weight of 750 mg/200 cm$^2$. This film adhesive sample was equilibrated at 25 Celsius and 50% relative humidity. The adhesion to steel value of this sample was measured at 4 N/25 mm.

Example 2

Preparation of a Backing Layer with an Absorbent Hydrophilic Adhesive Adhered Thereto A 1.75 mm-thick absorbent hydrophilic adhesive was prepared as described in Example 3 of International Publication No. WO 2009/091682. A continuous layer of the absorbent hydrophilic adhesive was laminated to a 23 micron thick film of Estane® 58237 thermoplastic polyurethane. This film adhesive sample was equilibrated at 25 Celsius and 50% relative humidity. The adhesion to steel value of this sample was measured at 5.8 N/25 mm.

Example 3

Preparation of a Porous Layer with a Hydrophobic Adhesive Coated Thereon

A 30 micron thick urethane film (Texin® 1209 thermoplastic polyurethane film from Bayer; Pittsburg, Pa.) was extruded onto a continuous acrylate adhesive whose coating weight was 550 mg/200 cm$^2$. A silicone gel adhesive was then coated at 0.1 mm thick and cured (as described in International Publication No. WO 2010/056543, which is incorporated herein by reference in its entirety) onto the urethane film/adhesive laminate. A protective liner put onto this silicone adhesive. This multilayer laminate was then mechanically perforated (1.5 mm diameter holes; 20% open). The acrylate side of the perforated laminate was then laminated to a polyurethane foam cut out of a 90642 3M™ Tegaderm™ Foam Silicone Border dressing (obtained from 3M Company; St. Paul, Minn.). The adhesion to steel of the silicone side of this foam laminate was then tested after equilibration of the foam laminate at 25 Celsius and 50% relative humidity. The adhesion to steel value was measured at 2 N/25 mm.

Example 4

Rheological Properties of the Absorbent Hydrophilic Adhesive Gel of the Present Disclosure A 1.6 mm-thick absorbent hydrophilic adhesive sample was prepared as described in as described in Example 3 of International Publication No. WO 2009/091682. The rheological properties of the absorbent hydrophilic adhesive were measured as a function of drying temperature and time using a TA Instruments' ARES rheometer (Texas Instruments, New Castle, Del.). Samples were dried at 48.9° C. The shear measurements were taken at 24° C. at a frequency range from 0.1 to 500 rad/second. The adhesive gel sample was a 25 mm diameter circle with a thickness of 1.6 mm. The results for the dynamic shear viscosity are shown in Table 1. The results of the storage shear modulus (G'), and the loss shear modulus (G") are shown in Table 2.

TABLE 1

Viscosity (poise) change with drying time at different shear rate.

| Drying time | Viscosity (Poise) | | |
| --- | --- | --- | --- |
| (days) | 1 rad/sec | 10 rad/sec | 100 rad/sec |
| 0 | 171000 | 28660 | 6299 |
| 1 | 215900 | 37350 | 8727 |
| 7 | 266300 | 50040 | 13330 |

TABLE 2

The change of the shear modulus (G') and the loss shear modulus (G") as a function of drying time and shear rate.

| Drying time (days) | G' and G" as a function of shear rate | | | | | |
|---|---|---|---|---|---|---|
| | 1 rad/sec | | 10 rad/sec | | 100 rad/sec | |
| | G' | G" | G' | G" | G' | G" |
| 0 | 150000 | 53000 | 245000 | 125000 | 500000 | 380000 |
| 1 | 200000 | 72000 | 325000 | 160000 | 650000 | 550000 |
| 7 | 235000 | 98000 | 420000 | 243000 | 910000 | 930000 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A wound dressing, comprising:
a moisture-transmissible backing layer having a first major surface, a second major surface, and a backing layer perimeter;
wherein the second major surface has a first hydrophobic adhesive disposed thereon proximate the backing layer perimeter;
an absorbent hydrophilic adhesive adhered to at least a portion of the second major surface of the backing layer, the absorbent hydrophilic adhesive comprising an absorbent hydrophilic adhesive perimeter, an absorbent hydrophilic adhesive first major surface, and an absorbent hydrophilic adhesive second major surface opposite the absorbent hydrophilic adhesive first major surface of the absorbent hydrophilic adhesive;
an antimicrobial agent dispersed throughout the absorbent hydrophilic adhesive;
a porous layer having a first side adhered to the absorbent hydrophilic adhesive second major surface, a second side, and a porous layer perimeter; and
a second hydrophobic adhesive adhered to the second side of the porous layer;
wherein 100% of the absorbent hydrophilic adhesive perimeter is overlapped by the backing layer and the entire absorbent hydrophilic adhesive perimeter extends beyond the porous layer perimeter toward the backing layer perimeter;
wherein at least 100% of the porous layer perimeter is overlapped by the absorbent hydrophilic adhesive.

2. The wound dressing of claim 1, wherein the absorbent hydrophilic adhesive has a thickness of 0.2 mm to 4.0 mm.

3. The wound dressing of claim 1, wherein the absorbent hydrophilic adhesive comprises less than 40% (w/w) water.

4. The wound dressing of claim 1, wherein the dressing further comprises a perforated layer disposed between the second side of the porous layer and the second hydrophobic adhesive.

5. The wound dressing of claim 4, wherein the perforated layer comprises a perforated polymeric substrate.

6. The wound dressing of claim 1, wherein adhesion to steel of the absorbent hydrophilic adhesive adhered to the backing layer is greater than adhesion to steel of the second hydrophobic adhesive adhered to the porous layer.

7. The wound dressing of claim 1, wherein adhesion to steel of the absorbent hydrophilic adhesive adhered to the backing layer is greater than adhesion to steel of the first hydrophobic adhesive adhered to the backing layer.

8. The wound dressing of claim 1, wherein the backing layer comprises a polymeric elastic film, an elastic nonwoven fabric, or combinations thereof.

9. The wound dressing of claim 8, wherein the backing layer is 15 μm to 250 μm thick.

10. The wound dressing of claim 1, wherein the backing layer has a Moisture Vapor Transmission Rate ≥10 g/10 cm$^2$/24 hours.

11. The wound dressing of claim 1, wherein the backing layer with the absorbent hydrophilic adhesive adhered thereto has a Moisture Vapor Transmission Rate ≥1 g/10 cm$^2$/24 hours.

12. The wound dressing of claim 1, wherein the absorbent hydrophilic adhesive has a shear modulus between 5,000 pascals and 50,000 pascals at 24° C. at a shear of 1 rad/sec.

13. The wound dressing of claim 1, wherein the absorbent hydrophilic adhesive has a loss shear modulus between 2,000 pascals and 20,000 pascals at 24° C. at a shear of 1 rad/sec.

14. The wound dressing of claim 1, wherein the porous layer comprises open-cell foam, a woven fabric, a nonwoven fabric, porous films, or a combination thereof.

15. The wound dressing of claim 1, wherein the absorbent hydrophilic adhesive is capable of absorbing ≥1.5 times its dry weight when contacted with an isotonic saline solution at 37° C. for 24 hours.

16. The wound dressing of claim 1, wherein the absorbent hydrophilic adhesive comprises crosslinked polyvinylpyrrolidone, polyglycerol-3, and water.

* * * * *

UNITED STATES PATENT AND TRADEMARK OFFICE
CERTIFICATE OF CORRECTION

PATENT NO. : 11,007,086 B2
APPLICATION NO. : 15/539866
DATED : May 18, 2021
INVENTOR(S) : David Holm It is certified that error appears in the above-identified patent and that said Letters Patent is hereby corrected as shown below:

In the Specification

<u>Column 5</u>
Line 13 (Approx.)    Delete "DeltStar" and insert -- DelStar --, therefor.

<u>Column 9</u>
Line 56              Delete "idodophors," and insert -- iodophors, --, therefor.

<u>Column 10</u>
Line 21              Delete "polyisprene" and insert -- polyisoprene --, therefor.
Line 25              Delete "Ac-Di-Solt" and insert -- Ac-Di-Sol® --, therefor.

<u>Column 12</u>
Line 4               Delete "idodophors;" and insert -- iodophors; --, therefor.
Line 26              Delete "g/cm$^2$," and insert -- g/cm$^3$, --, therefor.

Signed and Sealed this
Seventh Day of September, 2021

Drew Hirshfeld
*Performing the Functions and Duties of the
Under Secretary of Commerce for Intellectual Property and
Director of the United States Patent and Trademark Office*